US010155932B2

(12) United States Patent
Gregersen

(10) Patent No.: US 10,155,932 B2
(45) Date of Patent: Dec. 18, 2018

(54) DECREASING POTENTIAL IATROGENIC RISKS ASSOCIATED WITH INFLUENZA VACCINES

(71) Applicant: Novartis AG, Basel (CH)

(72) Inventor: Jens-Peter Gregersen, Marburg (DE)

(73) Assignee: Novartis AG, Basel (CH)

( * ) Notice: Subject to any disclaimer, the term of this patent is extended or adjusted under 35 U.S.C. 154(b) by 4 days.

(21) Appl. No.: 15/150,214

(22) Filed: May 9, 2016

(65) Prior Publication Data

US 2016/0251631 A1    Sep. 1, 2016

Related U.S. Application Data

(63) Continuation of application No. 13/740,100, filed on Jan. 11, 2013, now Pat. No. 9,358,280, which is a continuation of application No. 13/738,929, filed on Jan. 10, 2013, now Pat. No. 8,460,914, which is a continuation of application No. 13/274,285, filed on Oct. 14, 2011, now Pat. No. 9,220,768, which is a continuation of application No. 11/662,481, filed as application No. PCT/IB2005/003266 on Sep. 9, 2005, now Pat. No. 8,119,337.

(30) Foreign Application Priority Data

Sep. 9, 2004    (EP) ..................... 04255471

(51) Int. Cl.
| | |
|---|---|
| *C12N 7/00* | (2006.01) |
| *A61K 39/145* | (2006.01) |
| *C12Q 1/70* | (2006.01) |
| *A61K 39/12* | (2006.01) |
| *G01N 33/569* | (2006.01) |

(52) U.S. Cl.
CPC .............. *C12N 7/00* (2013.01); *A61K 39/12* (2013.01); *A61K 39/145* (2013.01); *C12Q 1/70* (2013.01); *C12Q 1/701* (2013.01); *G01N 33/56983* (2013.01); *C12N 2760/16034* (2013.01); *C12N 2760/16051* (2013.01); *C12N 2760/16134* (2013.01); *C12N 2760/16234* (2013.01); *G01N 2333/11* (2013.01)

(58) Field of Classification Search
None
See application file for complete search history.

(56) References Cited

U.S. PATENT DOCUMENTS

| | | | |
|---|---|---|---|
| 4,193,991 | A | 3/1980 | Appel et al. |
| 5,804,195 | A | 9/1998 | Gutter |
| 6,146,873 | A | 11/2000 | Kistner et al. |
| 6,344,354 | B1 | 2/2002 | Webster et al. |
| 6,855,544 | B1 * | 2/2005 | Hateboer ............ C07K 14/005 435/320.1 |
| 7,192,759 | B1 | 3/2007 | Pau et al. |
| 8,119,337 | B2 | 2/2012 | Gregersen |
| 2002/0106639 | A1 | 8/2002 | Wang et al. |
| 2005/0019891 | A1 | 1/2005 | Fouchier et al. |
| 2005/0118698 | A1 | 6/2005 | Vorlop et al. |

FOREIGN PATENT DOCUMENTS

| | | |
|---|---|---|
| EP | 1108787 A | 6/2001 |
| WO | WO-80/01243 A1 | 6/1980 |
| WO | WO-99/29717 A2 | 6/1999 |
| WO | WO 01/38362 A2 * | 5/2001 |
| WO | WO-03/023025 A1 | 3/2003 |
| WO | WO-2006/027698 A1 | 3/2006 |
| WO | WO-2008/175236 A1 | 12/2008 |

OTHER PUBLICATIONS

Bauer et al., Biologicals, 2004, 32:177-182. (Year: 2004).*
FDA Document, Points to Consider in the Manufacture and Testing of Monoclonal Antibody Products for Human Use, U.S. Department of Health and Human Services, FDA, Center for Biologics Evaluation and Research, 1997, 50 pages. (Year: 1997).*
Norman et al., J. Clin. Invest., Apr. 2000, 105(8):1035-1038. (Year: 2000).*
"Table of Extraneous Agents to be Tested for in relation to the General and Species Specific Guidelines on Production and Control of Mammalian Veterinary Vaccines," Legislative Basis Directive 81/852/EEC as amended, Date of First Adoption prior to Sep. 1994, Date of Entry into Force prior to Sep. 1994, Status Last revised Sep. 1994. 8 pages.
Ahn et al. (Jun. 2004). "Susceptibility of mouse primary cortical neuronal cells to coxsackievirus B," J Gen Virol. 85(Pt 6):1555-64.
Allan et al. (1994). "Production, preliminary characterisation and applications of monoclonal antibodies to porcine circovirus," Vet Immunol Immunopathol. 43(4):357-71.
Allan et al. (1994). "Some biological and physic-chemical properties of porcine circovirus," J Vet Med B 41:17-26.
Allan et al. (2000). "Porcine circovi uses: a review," J Vet Diagn Invest 12:3-14.
Azetaka et al. (1981). "Studies on canine parvovirus isolation, experimental infection and serological survey," Jpn J Vet Sci 43:243-255.
Bailey (Apr. 2011). "Contamination Control: Learning from Experience," ViruSure publication, 4 pages.
Brands et al. (1997). "Influvac<sup>JC</sup>: A safe Madin Darby Canine Kidney (MDCK) ell culture-based influenza vaccine," Dev. Biol. Stand. 98:93-100.
Browne et al. (May 1981). "Comparative inhibition of influenza and parainfluenza virus replication by ribavirin in MDCK cells," Antimicrob Agents Chemother. 19(5): 712-715.

(Continued)

Primary Examiner — Stacy B Chen
(74) Attorney, Agent, or Firm — Morrison & Foerster LLP

(57) ABSTRACT

Influenza viruses for use in preparing human vaccines have traditionally been grown on embryonated hen eggs, although more modern techniques grow the virus in mammalian cell culture e.g. on Vero, MDCK or PER.C6 cell lines. The inventor has realised that the conditions used for influenza virus culture can increase the risk that pathogens other than influenza virus may grow in the cell lines and have identified specific contamination risks. Suitable tests can thus be performed during manufacture in order to ensure safety and avoid iatrogenic infections.

20 Claims, No Drawings

(56) References Cited

OTHER PUBLICATIONS

Cirone et al. (2004). "Immunogenicity of an inactivated oil-emulsion canine distemper vaccine in African wild dogs," J Wild Dis 40(2):343-346.
Cohen et al. (Sep. 1997). "Varicella-zoster virus glycoprotein I is essential for growth of virus in Vero cells," J Virol. 71(9): 6913-6920.
CPMP/BWP/214/96 (Mar. 12, 1997). Committee for proprietary medicinal products (CPMP). Note for guidance on harmonisation of requirements for influenza vaccines.
CPMP/BWP/2490/00 (Jan. 17, 2002). Committee for proprietary medicinal products (CPMP). Cell culture inactivated influenza vaccines, annex to note for guidance on harmonisation of requirements for influenza vaccines CPMP/BWP/214/96.
CPMP/BWP/268/95 (Feb. 14, 1996). Committee for proprietary medicinal products (CPMP). Note for guidance on virus validation studies: the design, contribution and interpretation of studies validating the inactivation and removal of viruses.
Curriculum Vitae of Carine Logvinoff. Filed in opposition against EP2578229, submitted Dec. 10, 2015, 9 pages.
Darling (May 2002). "Validation of biopharmaceutical purification processes for virus clearance evaluation," Mol Biotechnol. 21(1):57-83.
Ellebedy et al. (2009). Vaccine 27:D65-D68.
European Agency for the Evaluation of Medicinal Products, Evaluation of Medicines for Human Use, Cell Culture Inactivated Influenza Vaccines, Annex to Note for Guidance on Harmonisation of Requirements for Influenza Vaccines (CPMP/BWP/214/96), Jan. 2002, available from the following website: http://www.ema.europa.eu/pdfs/human/bwp/249000en.pdf.
European Agency for the Evaluation of Medicinal Products, Evaluation of Medicines for Human Use, Cell Culture Inactivated Influenza Vaccines, Note for Guidance on Quality of Biotechnological Products: Viral Safety Evaluation of Biotechnology Products Derived from Cell Lines of Human or Animal Origin. (CPMP/ICH/295/95), Oct. 1997.
European Agency for the Evaluation of Medicinal Products, Evaluation of Medicines for Human Use, Cell Culture Inactivated Influenza Vaccines, Note for Guidance on Quality of Biotechnological Products: Derivation and Characterisation of Cell Substrates Used for Production of Biotechnological/Biological Products. (CPMP/ICH/294/95), Mar. 1998.
European Pharmacopoeia 5.0, section 5.2.2. (Published Jun. 2004, entry into force Jan. 2005). Chicken flocks free from specified pathogens for the production and quality control of vaccines.
European Pharmacopoeia. Excerpt from the website <http://www.chemeurope.com/en/encyclopedia/European_Pharmacopoeia.html>, Feb. 18, 2013.
European Pharmacopoeia. Excerpt from the website <http://www.tsoshop.co.uk/bookstore.asp?F0=1160676&ProductiD=9789287158437&Action=Book?>, Feb. 18, 2013.
Excerpts from European Pharmacopoeia 5.0, (Published Jun. 2004), pp. 177-183, 458-462, and 590-595, available at < http://lib.njutcm.edu.cn/yaodian/ep/EP5.0/ >.
Fernandez-Arias et al. (1997) "The major antigenic protein of infectious bursal disease virus, VP2, is an apoptotic inducer," Journal of Virology 71(10):8014-8018.
Fields Virology, Fourth Edition, 2001, Lippincott Williams & Wilkins Publishers, Philadelphia, chapter 18 "Diagnostic Virology", pp. 493-531.
Fields Virology, Fourth Edition, 2001, Lippincott Williams & Wilkins Publishers, Philadelphia, chapter 64 "Human Polyomavirus", pp. 2175-2196.
Fields Virology, Third Edition, 1996, Lippincott-Raven Publishers, Philadelphia, chapter 64, "Polyomaviruses", pp. 2027-2029.
Govorkova et al. (1999). "Growth and immunogenicity of influenza viruses cultivated in Vero or MDCK cells and in embryonated chicken eggs," Dev Biol Stand, 98:39-51.
Gregersen (2008) "A risk-assessment model to rate the occurrence and relevance of adventitious agents in the production of influenza vaccines," Vaccine 26(26):3297-304.
Gregersen (2008). "A quantitative risk assessment of exposure to adventitious agents in a cell culture-derived subunit influenza vaccine," Vaccine, 26(26):3332-40.
Gruber et al., The Journal of Infectious Diseases, 1993, 168:53-60.
Gwaltney, Jr. (1997). Viral Infections of Humans: Epidemiology and Control, Chapter 26, Rhinoviruses. 3 pages.
Gwaltney, Jr. et al. (1964) "Rhinoviruses and Respiratory Disease," Bacteriological Reviews 28(4):409-422.
Hattermann et al. (2004). "Infection studies on human cell lines with porcine circovirus type 1 and porcine circovirus type 2," Xenotransplantation. 11(3):284-94.
Horaud (Jan. 1, 1992) "Absence of viral sequences in the WHO-Vero Cell Bank. A collaborative study," Dev Biol Stand 76:43-6.
Hütter et al. (2013). "Toward animal cell culture-based influenza vaccine design: viral hemagglutinin N-glycosylation markedly impacts immunogenicity," J Immunol, 190(1):220-30.
Interlocutory decision in opposition proceedings, filed in opposition against EP2236155, dated May 8, 2015, 13 pages.
Kaygusuz et al. (Apr. 2004). "Investigation of atypical bacteria and virus antigens in respiratory tract infections by use of an immunofluorescence method," Jpn J Infect Dis. 57(2):33-6.
Kim (Nov. 1999). "Application of reverse transcription polymerase chain reaction to detect porcine epidemic diarrhea virus in Vera cell culture," J Vet Diagn Invest. 11 (6):537-8.
Kim et al. (2004) "Orthoreovirus and Aquareovirus core proteins: conserved enzymatic surfaces, but not protein-protein interfaces," Virus Research 101:15-28.
Kistner et al. (1998) Vaccine 16(9-10):960-968.
Kitamura et al. (1994). "Transmission of the human polyomavirus JC virus occurs both within the family and outside the family," J Clin Microbiol, 32(10):2359-63.
Lai et al. (2000) "Generation and characterization of a hepatitis C virus NS3 protease-dependent bovine viral diarrhea virus," J Virol 74(14):6339-47.
Levandowski, R (1999). "Regulatory perspective in the United States on cell cultures for production of inactivated influenza virus vaccines," Dev. Biol. Stand. 98:171-175.
Lovatt (2002). "Applications of quantitative PCR in the biosafety and genetic stability assessment of biotechnology products," J Biotechnol 82:279-300.
Meng et al. (Apr. 1993). "Development of a radiolabeled nucleic acid probe for the detection of encephalomyocarditis virus of swine," J Vet Diagn Invest. 5(2):254-8.
Merten (Jul. 2002). "Virus contaminations of cell cultures—A biotechnological view," Cytotechnology. 39(2):91-116.
Monath et al. (2004). "ACAM2000 clonal Vero cell culture vaccinia virus (New York City Board of Health strain)—a second-generation smallpox vaccine for biological defense," Int J Infect Dis 8Supp2:S31-S44.
Moriuchi et al. (Jun. 1990). "Human malignant melanoma cell line (HMV-II) for isolation of influenza C and parainfluenza viruses," J Clin Microbiol. 28(6):1147-50.
Munch et al, "Detection and subtyping (H5 and H7) of avian type A influenza virus by reverse transcription-PCR and PCR-ELISA." Archives of Virology, 2001, 146:87-97.
Murakami et al. (2012). "Enhanced growth of influenza vaccine seed viruses in vero cells mediated by broadening the optimal pH range for virus membrane fusion," J Virol, 86(3):1405-10.
Nagarajan et al. (Apr. 2001). "Selection of an infectious bursal disease virus mutant with increased immunogenicity following passage under humoral immune pressure," Can J Vet Res. 65(2):89-96.
Ng et al. (Dec. 2003). "Proliferative growth of Sars coronavirus in Vero E6 cells," J Gen Virol. 84(Pt 12):3291-303.
Niizuma et al. (May 2003). "Construction of varicella-zoster virus recombinants from parent Oka cosmids and demonstration that ORF65 protein is dispensable for infection of human skin and T cells in the SCID-hu mouse model," J Viral. 77(1 0):6062-5.

(56) References Cited

OTHER PUBLICATIONS

Nishio et al. (1990). "Antiviral effect of 6-diazo-5-oxo-L-norleucine, antagonist of gamma-glutamyl transpeptidase, on replication of human parainfluenza virus type 2," J Gen Virol. 71 (Pt 1):61-7.
Norrby et al. (Aug. 1970). "Morphogenesis of respiratory syncytial virus in a green monkey kidney cell line (Vero)," J Virol. 6(2):237-42.
Notice of Opposition against EP-2236155-61, filed on Feb. 18, 2013.
Notice of Opposition filed on Apr. 10, 2014, by Merck & Co., Inc., for EP2578229, 25 pages.
Notice of Opposition filed on Apr. 10, 2014, by MSD Animal Health, for EP2578229, 28 pages.
Notice of Opposition filed on Apr. 9, 2014, by Sanofi Pasteur, for EP2578229, 43 pages.
Numazaki et al. (1987). "A microplate method for isolation of viruses from infants and children with acute respiratory infections," Microbiol Immunol. 31(11):1085-95.
Ohnishi et al. (Aug. 1982). "Antiviral activity of sodium 5-aminosulfonyl-2,4-dichlorobenzoate (M12325)," Antimicrob Agents Chemother. 22(2):250-4.
Opponent's Response, filed in opposition against EP2578229, dated Dec. 10 2015, 26 pages.
Padgett et al. (1977). "JC Virus, a Human Polyomavirus Associated with Progressive Multifocal Leukoencephalopathy : Additional Biological Characteristics and Antigenic Relationships," Infection and Immunity, American Society for Microbiology. 15(2): 656-662.
Partial European Search Report dated May 9, 2012, for EP Application No. 12157945 filed Mar. 2, 2012, 5 pages.
Patentee's Response to Appeal, filed during opposition against EP2236155, dated Feb. 5, 2016, 12 pages.
Payne (Sep. 13, 2012). "Eggs in Virology" In: Carter, T.C. (Ed.): "Egg Quality, A Study of the Hen's Egg", Oliver & Boyd, Edinburgh, pp. 181-203.
Pennathur et al. (Dec. 2003). "Evaluation of attenuation, immunogenicity and efficacy of a bovine parainfluenza virus type 3 (PIV-3) vaccine and a recombinant chimeric bovine/human PIV-3 vaccine vector in rhesus monkeys," J Gen Virol. 84(Pt 12):3253-61.
Potts et al. (2000). "Detecting and removing porcine viruses," Biopharm International, 7 pages.
Racaniello (2001). "Picornaviridae: The viruses and Their Replication," Chapter 23 in "Fields Virology," vol. 2, Knipe et al (Eds), Lippincott Williams & Wilkins, Philadelphia, PA.
Reina et al. (Dec. 2001). "Evaluation of different continuous cell lines in the isolation of mumps virus by the shell vial method from clinical samples," J Clin Pathol. 54(12):924-6.
Response by Opponent, filed in opposition against EP2236155, dated Dec. 22, 2014, 15 pages.
Response by Sanofi Pasteur, filed in opposition against EP2578229, dated Apr. 27, 2015, 19 pages.
Response by the Patentee, filed during prosecution of EP2578229, dated Mar. 22, 2013, 21 pages.
Response by the Patentee, filed during prosecution of US 2012-034600, related to EP 2578229, dated Sep. 12, 2012, 13 pages.
Response by the Patentee, filed in opposition against EP2578229, dated Dec. 9, 2015, 6 pages.
Response to Notice of Opposition, filed in opposition against EP2578229, dated Oct. 20, 2014, 10 pages.
Response to Notice of Opposition, filed in opposition against EP2236155, dated Oct. 1, 2013, 8 pages.
Roberts et al. (Apr. 1995). "Respiratory syncytial virus matures at the apical surfaces of polarized epithelial cells," J Virol. 69(4):2667-2673.
Robertson (1999). "An overview of host cell selection," Dev Biol Stand, 98:7-11.
Rogers et al. (Jul. 1999). "Conjunctivitis caused by a swine Chlamydia trachomatis-like organism in gnotobiotic pigs," J Vet Diagn Invest. 11(4):341-4.
Romanova et al. (2003). "Distinct host range of influenza H3N2 virus isolates in Vero and MDCK cells is determined by cell specific glycosylation pattern," Virology, 307(1):90-7.
Romanova et al. (2004). "Live cold-adapted influenza A vaccine produced in Vero cell line," Virus Research 103:187-193.
Sears et al. (Jun. 1991). "Infection of polarized MDCK cells with herpes simplex virus 1: two asymmetrically distributed cell receptors interact with different viral proteins," Proc Natl Acad Sci USA. 88(12):5087-91.
Seehafer et al. (Feb. 1978). "Observations on the growth and plaque assay of BK virus in cultured human and monkey cells," J Gen Virol. 38(2):383-7.
Sends et al. (1995). "Detection by PCR of wild-type canine parvovirus which contaminates dog vaccines," J Clin Microbiol 33(1):110-3.
Sheets, Rebecca (2000). "History and characterization of the vero cell line," Vaccines and Related Biological Products Advisory Meeting, held on May 12, 2000, 12 pages.
Shibata et al. (Mar. 2003). "PCR detection of Porcine circovirus type 2 DNA in whole blood, serum, oropharyngeal swab, nasal swab, and feces from experimentally infected pigs and field cases," J Vet Med Sci. 65(3):405-8.
Shimokata et al. (Jun. 1980). "Influence of trypsin on the infectivity and biological properties or parainfluenza type 2 type 2 (croup-associated) virus in Vero cells," J Gen Virol. 48(Pt 2):407-10.
Statement of Grounds of Appeal, filed in opposition against EP2236155, dated Sep. 18, 2015, 14 pages.
Stuart et al. (Aug. 2002). "Determination of the structure of a decay accelerating factor-binding clinical isolate of echovirus 11 allows mapping of mutants with altered receptor requirements for infection," J Virol. 76(15):7694-704.
Swayne et al. (May 2004). "Domestic poultry and SARS coronavirus, southern China," Emerg Infect Dis. 10(5):914-6.
Syrmis et al. (May 2004). "A sensitive, specific, and cost-effective multiplex reverse transcriptase-PCR assay for the detection of seven common respiratory viruses in respiratory samples," J Mol Diagn. 6(2):125-31.
Tischer et al. (1987). "Replication of porcine circovirus: induction by glucosamine and cell cycle dependence," Arch Virol, 96(1-2)29-57.
Todd (2000). "Circoviruses: immunosuppressive threats to avian species: a review," Avian Pathol. Oct;29(5):373-94.
Todd (Feb. 2004) "Avian circovirus diseases: lessons for the study of PMWS," Veterinary Microbiology 98:169-174.
Tran et al. (Jan. 2004). "Effects of altering the transcription termination signals of respiratory syncytial virus on viral gene expression and growth in vitro and in vivo," J Virol. 78(2):692-9.
Trlifajová et al. (1984). "Isolation of varicella-zoster virus from pharyngeal and nasal swabs in varicella patients," J Hyg Epidemiol Microbiol Immunol. 28(2):201-6.
Uwatoko et al. (1996). "Canine parvovirus binds to multiple cellular membrane proteins from both permissive and nonpermissive cell lines," Vet Microbiol 51:267-273.
Wessman et al. (1999). "Benefits and risks due to animal serum used in cell culture production," Dev Biol Stand, 99:3-8.
WHO technical Report Series. (1998). "Requirement for the use of animal cells as in vitro substrates for the production of biologicals (Requirements for biological substances No. 50)," World Health Organization, Annex 1, No. 878, pp. 19-56.
WHO technical Report Series. (2002). "Recommendations for the production and control of poliomyelitis vaccine (inactivated)," World Health Organization, Annex 2, No. 910, pp. 32-65.
WHO Technical Report Series. (Jan. 1, 2003). "Recommendations for Production and Control of Influenza Vaccine (Inactivated)." Retrieved from <http://www.who.int/biologicals/publications/trs/areas/vaccines/influenza/recommen_influenza_vaccine_nov_2003.pdf>.
Wikipedia. "European Pharmacopoeia." Retrieved from <http://en.wikipedia.orglwiki/European_Pharmacopoeia>, accessed Feb. 18, 2013.
Wisher, Martin (2002). "Biosafety and product release testing issues relevant to replication-competent oncolytic viruses," Cancer Gene Therapy 9:1056-1061.

(56) References Cited

OTHER PUBLICATIONS

Wu et al. (Jul. 2004). "Inhibition of severe acute respiratory syndrome coronavirus replication by niclosamide," Antimicrob Agents Chemother. 48(7):2693-6.

Zhang et al. (Aug. 2003). "Inhibiting severe acute respiratory syndrome-associated coronavirus by small interfering RNA," Chin Med J (Engl). 116(8):1262-4.

Affidavit of John Petricciani, filed in relation to EP2578229, dated Nov. 14, 2016, 6 pages.

Anonymous (2003). "Substances of human or animal origin for pharmeutical use", pharmeuropa, vol. 15, No. 2, 1 page.

Curriculum vitae of John Petricciani, filed in relation to EP2578229, submitted Nov. 18, 2016, 3 pages.

Opposition Decision Revoking the European Patent, filed in relation to EP2578229, dated Apr. 12, 2017, 35 pages.

Mallet et al. (2014). "Need for New Technologies for Detection of Adventitious Agents in Vaccines and Other Biological Products," PDA J Pharm Sci Technol. 68:556-562.

Notice of Appeal, filed in relation to EP2578229, dated Jun. 20, 2017, 1 page.

Submissions under rule 116 EPC, filed in relation to EP2578229, dated Nov. 2016, 8 pages.

Victoria et al. (2010). "Viral nucleic acids in live-attenuated vaccines: detection of minority variants and an adventitious virus," J Virol. 84(12):6033-40.

Pau et al. (2001). "The human cell line PER.C6 provides a new manufacturing system for the production of influenza vaccines," Vaccine, 19: 2716-2721.

European Medicines Agency, (2013). "Guideline on the use of porcine trypsin used in the manufacture of human biological medicinal products," (EMA/CHMP/BWP/814397/2011), pp. 1-8.

Henchal, Laraine S. (2008). "Review of Vero Cell Banks used for Vaccine Production and Adventitious Agent Testing of Virus Seeds and Vaccine Human Rotavirus Vaccine (HRV)—Rotarix," Memorandum, 12 pages.

Statement of Grounds of Appeal, filed in opposition against EP2578229, dated Aug. 22, 2017, 8 pages.

Opponent's Response to the Patentee's Grounds of Appeal, filed in the Opposition against EP2578229 on Dec. 21, 2017, 16 pages.

Anonymous. Technical Sheet: Reovirus (REO-3)—Charles River Research Animal Diagnostic Service. (2009), 1 page.

Japan Ministry of Health and Welfare, Notice 1314 of the Director-General of Pharmaceutical and Medical Safety Bureau (Dec. 26, 2000). "Ensuring the quality and safety of pharmaceuticals manufactured using human- or animal- derived ingredients as raw materials," 25 pages.

Opponent's Response to the Patentee's Grounds of Appeal, filed in the Opposition against EP2578229 on Dec. 26, 2017, 128 pages (includes English translation).

\* cited by examiner

DECREASING POTENTIAL IATROGENIC RISKS ASSOCIATED WITH INFLUENZA VACCINES

CROSS REFERENCE TO RELATED APPLICATIONS

This application is a Continuation of U.S. patent application Ser. No. 13/740,100, filed Jan. 11, 2013, which is a Continuation of U.S. patent application Ser. No. 13/738,929, filed Jan. 10, 2013, now U.S. Pat. No. 8,460,914, which is a Continuation of U.S. patent application Ser. No. 13/274,285, filed Oct. 14, 2011, now U.S. Pat. No. 9,220,768, which is a Continuation of U.S. patent application Ser. No. 11/662,481, with an international filing date of Sep. 9, 2005, now U.S. Pat. No. 8,119,337, which is a U.S. National Phase patent application of PCT/IB2005/003266, filed Sep. 9, 2005, which claims priority to European Patent Office (EPO) patent application Serial No. 04255471.7, filed Sep. 9, 2004, all of which are hereby incorporated by reference in the present disclosure in their entirety.

TECHNICAL FIELD

This invention concerns the production and quality control of influenza virus vaccines.

BACKGROUND ART

Influenza viruses for use in preparing human vaccines have traditionally been grown on embryonated hen eggs, although more modern techniques grow the virus in mammalian cell culture e.g. on Vero cells, MDCK cells or PER.C6 cells. The change in virus growth substrate has provided an opportunity for regulatory re-assessment of influenza vaccine safety. For example, contamination with host cell DNA has been a regulatory concern for the cell-derived vaccines [1], but has not been of concern in the past for vaccines grown in eggs.

The safety issues surrounding egg-derived influenza vaccines are thus different from those surrounding vaccines grown in cell culture, with cell-derived vaccines being under closer scrutiny. It is an object of the invention to address these different safety issues, and in particular to provide methods for enhancing the safety of influenza vaccines grown on cell culture.

DISCLOSURE OF THE INVENTION

By definition, the use of mammalian cell substrates for influenza vaccine production involves culturing the cells under conditions that are well suited to viral growth and replication. The inventor has realised that these conditions increase the risk that pathogens other than influenza virus may grow in the cell culture, thereby leading to potential contamination of the final vaccine product. Tests for contamination are generally not difficult to perform, but a manufacturer first has to know what tests to perform. The inventor has identified specific contamination risks, and their work means that suitable tests can be performed during manufacture in order to ensure the safety and quality of influenza vaccines grown on cell culture. Some of the contaminants may be harmless in a final vaccine product, but their presence can interfere with influenza virus propagation and downstream purification, and so their removal is primarily of concern for quality and reproducibility; other contaminants would be harmful in a final vaccine, and so their removal is primarily a safety concern.

The risk of contamination arising from viral co-culture is not without precedent (e.g. certain early poliovirus vaccine batches were contaminated by simian virus 40 ('SV40'), a polyomavirus), but there have not been any previous disclosures on identifying specific risks associated with cell culture for human influenza vaccine production. Influenza viruses grown on cell culture are at particular risk from contamination because the strains used for vaccine production are changed every year, and so new cultures have to be established every year. This annual change in production materials means that every new year brings a new risk of contamination, particularly as multiple passages are involved during preparation of seed viruses for manufacturers, thereby increasing the risk of parallel growth of adventitious pathogenic agents.

The inventor has identified infectious agents that can grow in the conditions used for growing influenza viruses in cell culture but that do not grow in hen eggs. These infectious agents represent a new contamination risk for influenza vaccines that was never of concern for traditional influenza vaccines. Thus the invention provides a process for preparing an influenza vaccine from influenza virus that has been grown in a culture of a mammalian cell line, comprising a step in which the vaccine and/or the culture is tested for the presence of an infectious agent that can grow in said cell line but that does not grow in embryonated hen eggs.

The inventor has also identified infectious agents that grow in some cell substrates used for influenza vaccine production but do not grow in others. These infectious agents are thus a contamination risk only for certain influenza vaccines. Thus the invention also provides a process for preparing an influenza vaccine from influenza virus that has been grown in a culture of a first mammalian cell line, comprising a step in which the vaccine and/or the culture is tested for the presence of an infectious agent that can grow in said first cell line but that does not grow in a second mammalian cell line.

The invention also provides a process for preparing an influenza vaccine from influenza virus that has been grown in a culture of a mammalian cell line, comprising a step in which the vaccine and/or the culture is treated to remove and/or inactivate an infectious agent that can grow in the cell line but does not grow in embryonated hen eggs. Similarly, the invention provides a process for preparing an influenza vaccine from influenza virus that has been grown in a culture of a first mammalian cell line, comprising a step in which the vaccine and/or the culture is treated to remove and/or inactivate an infectious agent that can grow in said first cell line but does not grow in a second mammalian cell line. After removal and/or inactivation, the vaccine/culture may be tested for the presence of the infectious agent e.g. to verify that it is has been removed/inactivated.

The invention also provides an influenza vaccine that has been obtained by a process of the invention. The invention also provides an influenza vaccine that is obtainable by a process of the invention.

The invention also provides an influenza vaccine that has been grown in a culture of a mammalian cell line, wherein the vaccine has been confirmed as free from the presence of an infectious agent that can grow in said cell line but that does not grow in embryonated hen eggs. Similarly, the invention provides an influenza vaccine that has been grown in a culture of a first mammalian cell line, wherein the vaccine has been confirmed as free from the presence of an infectious agent that can grow in said first cell line but that does not grow in a second mammalian cell line.

The invention also provides an influenza vaccine in which mammalian reovirus is undetectable by RT-PCR (e.g. using the L1-based RT-PCR technique disclosed in reference 16, using primers L1.rv5, L1.rv6, L1.rv7 and LV1.rv8 as taught). Not having been grown on eggs, the vaccine will be free from ovalbumin and from chicken DNA.

The Mammalian Cell Line

The influenza vaccines of the invention are grown in mammalian cell lines, rather than being grown in embryonated eggs. Typical mammalian cell lines used in production of biologicals include: MDCK; CHO; BHK; Vero; MRC-5; PER.C6; WI-38; etc.. Preferred mammalian cell lines for growing influenza viruses include: MDCK cells [2-5], derived from Madin Darby canine kidney; Vero cells [6-8], derived from African green monkey (*Cercopithecus aethiops*) kidney; or PER.C6 cells [9], derived from human embryonic retinoblasts.

These cell lines are widely available e.g. from the American Type Cell Culture (ATCC) collection [10], or from the Coriell Cell Repositories [11]. For example, the ATCC supplies various different Vero cells under catalog numbers CCL-81, CCL-81.2, CRL-1586 and CRL-1587, and it supplies MDCK cells under catalog number CCL-34.

As well as being useful for material derived from growth on mammalian cell lines, the invention can also be extended for material derived from growth on avian cell lines [e.g. refs. 12 & 13], including cell lines derived from hens e.g. chicken embryo fibroblasts (CEF), etc.

Infectious Agents That Do Not Grow in Embryonated Hen Eggs

The inventor has identified a variety of pathogens that can grow in mammalian cell lines (in particular in both MDCK cells and Vero cells) used for preparing influenza virus for vaccine production but that do not grow in hen eggs. Testing for contamination by these pathogens was not necessary for vaccines prepared on the traditional egg substrate, but the inventor has realised that vaccine quality control should include tests for one or more of these pathogens in order to ensure the highest safety standards. The pathogens are as follows:

- Pneumovirinae, such as the *Pneumovirus* genus, including respiratory syncytial virus (RSV).
- *Morbilliviruses* of the Paramyxoviridae family, such as measles virus.
- *Enteroviruses* of the Picornaviridae family, such as Coxsackie viruses, echoviruses and enteroviruses, although some Coxsackie viruses (e.g. B3, B4) have been found not to grow in MDCK cells.
- Mammalian Reoviridae, in particular orthoreoviruses (e.g. mammalian reoviruses) and rotaviruses. Reoviruses can show unrestricted growth in Vero and MDCK cells, and so testing for them is of particular importance. Rotaviruses share the protease requirements of influenza viruses in order to grow in cell culture, and this parallel could unwittingly lead to activation of contaminating rotaviruses.

Where these pathogens have different strains that have different hosts (e.g. human RSV and bovine RSV), the test will typically concern strain(s) that can infect humans Testing for these agents is particularly important for viral strains derived by reverse genetics techniques, as seed viruses for virus manufacture will have undergone multiple passages in mammalian cell culture during the reverse genetics procedure, thereby increasing the risk of contamination by adventitious infective agents.

Infectious Agents That Do Not Grow in Eggs, But Grow in Different Mammalian Cell Lines The inventor has identified a variety of pathogens that do not grow in hen eggs, do not grow in MDCK cells, but do grow in Vero cells. Testing for contamination by these pathogens was not necessary for vaccines prepared on the traditional egg substrate and is not necessary for vaccines prepared on MDCK cells, but the inventor has realised that quality control of vaccines grown on Vero cells should include tests for one or more of these pathogens in order to ensure the highest safety standards. The pathogens are as follows:

- *Metapneumoviruses* of the Paramyxoviridae family, such as human metapneumovirus (HMPV).
- *Rubulaviruses* of the Paramyxoviridae family, such as mumps virus, which grows well in Vero.
- Togaviridae, such as *Rubellavirus.*
- Coronaviridae, such as the SARS coronavirus and other human coronaviruses. These viruses show high growth levels in Vero cells, with the SARS virus showing unrestricted growth, and so testing for them is of particular importance.
- *Rhinoviruses* of the Picornaviridae family, such as M-strains of *Rhinovirus.*
- Varicella Zoster virus (VZV), also known as human herpes virus 2 (HHV3). VZV can show unrestricted growth in Vero cells, and so testing for it is of particular importance.
- Polyomaviridae, such as the SV-40 polyomavirus, the BK polyomavirus and the JC polyomavirus. These polyomaviruses can show unrestricted growth in Vero cells (particularly BK cells), and so testing for them is of particular importance.
- Porcine circoviruses.
- Porcine picornaviruses, such as swine vesicular disease virus (SVDV) and Teschen-Talfan virus.
- *Chlamydia* bacteria, including *C. trachomatis, C. pneumoniae* and *C. psittaci.* These bacteria may grow in Vero cells, and so testing for them is of particular importance.
- *Parvoviruses* such as canine parvovirus (CPV) or porcine parvoviruses.

Where these pathogens have different strains that have different hosts (e.g. human RSV and bovine RSV), the test will typically concern strain(s) that can infect humans Testing for non-human viruses (e.g. avian and porcine viruses) is mainly of concern only when avian or porcine materials have been used in viral preparation e.g. if strains were initially isolated from pigs or birds, or if egg passages were used during initial growth, or if porcine trypsin was used in cell culture, etc.

Infectious Agents That Grow in Eggs and Mammalian Cell Lines

The inventor has also identified pathogens that, in contrast to those described above, grow both in mammalian cell lines and in hens eggs. A process of the invention may involve a step of testing for such pathogens, but this step would also be part of enhanced quality control of viruses grown in hens eggs. These pathogens include:

- Parainfluenza viruses (PIV), members of the Paramyxoviridae paramyxovirinae, including PIV-1, PIV-2 and PIV-3.
- The Herpesviridae, such as herpes simplex virus 1 and 2.
- The Adenoviridae, such as the adenoviruses, including human and simian adenovirus.
- *Mycoplasma.*
- Avian circoviruses.

Avian Reoviridae, in particular orthoreoviruses, such as avian reoviruses that can grow in mammalian cell lines.

The inventor has also identified pathogens that grow in hen eggs and in Vero cells, but do not or are unlikely to grow in MDCK cells. A process of the invention may involve a step of testing for such pathogens, but this step would also be part of enhanced quality control of viruses grown in hens eggs, and the step is not necessary if a MDCK substrate is used. These pathogens include:

Birnaviridae, such as infectious bursal disease virus (also known as gumboro virus).

Testing for agents that grow in both eggs and cell lines is important for viral strains derived after multiple passages in eggs e.g. seed viruses for virus manufacture.

As these pathogens grow in eggs then testing for their presence can also be used for viruses prepared from viruses grown on eggs. Thus the invention is not limited to vaccines grown on cell culture, but can also be used for 'traditional' egg-based vaccines.

Testing Methods

Methods for detecting the presence of pathogens in cell cultures and in biopharmaceuticals are routinely available. Methods will generally rely on immunochemical detection (immunoassay, western blot, ELISA, etc.) and/or on nucleic acid detection (hybridisation methods, such as Southern blots or slot blots, PCR, etc.). As an alternative, it is possible to test for the presence of a pathogen by conventional cell culture inoculation (i.e test whether the material leads to production of the contaminating pathogen when cultured under suitable conditions).

Methods may detect a single pathogen (e.g. virus) or may detect multiple pathogens (e.g. viruses). Where a test detects multiple pathogens (e.g. 'X', 'Y' or 'Z') then it may give a specific result (e.g. virus 'Y' is present) or it may give a general result (e.g. one of 'X', 'Y' or 'Z' is present). Methods may be quantitative, semi-quantitative or qualitative. Real-time detection methods may be used.

General guidance for detecting a pathogen (e.g. virus) of interest can be found in reference 14. A number of more specific assays are given in the following paragraph, and the skilled person can readily find or prepare an assay for detecting the presence of any chosen pathogen.

Reference 15 discloses a multiplex reverse transcription PCR (RT-PCR) assay, referred to as 'm-RT-PCR-ELISA', for the detection of nine respiratory tract pathogens in a single test, namely: enterovirus, influenza virus type A and type B, respiratory syncytial virus, parainfluenzavirus type 1 and type 3, adenovirus, *Mycoplasma pneumoniae* and *Chlamydia pneumoniae*. A RT-PCR method for detecting mammalian reovirus is disclosed in reference 16. Reference 17 discloses a real-time RT-PCR assay for detecting human metapneumoviruses from all known genetic lineages. Reference 18 discloses a single RT-PCR assay for detection of human respiratory syncytial virus (HRSV), human parainfluenzaviruses 1, 2, & 3 and influenza A & B. Reference 19 discloses a multiplex RT-PCR assay to detect and differentiate measles virus, rubella virus, and parvovirus B19. A real-time RT-PCR assay to detect human rhinovirus with accurate discrimination from other viruses from the family Picornaviridae is disclosed in reference 20. Reference 21 discloses a multiplex RT-PCR assay with nested primer sets targeted to conserved regions of human parainfluenza virus haemagglutinin, human coronavirus spike protein, and human enterovirus and rhinovirus polyprotein genes, which permits rapid, sensitive, and simultaneous detection and typing of the four types of parainfluenza viruses (1, 2, 3, 4AB), human coronavirus 229E and OC43, and the generic detection of enteroviruses and rhinoviruses. SVDV detection by RT-PCR is disclosed in reference 22. A one step quantitative RT-PCR assay for the SARS coronavirus is disclosed in reference 23. Reference 24 discloses a TaqMan allelic discrimination real-time PCR assay for VZV. A multiplex PCR assay for rapid simultaneous detection of pseudorabies viruses, parvoviruses and circoviruses is disclosed in reference 25. A real-time FRET probe PCR assay for SV-40 polyomavirus detection is described in reference 26. Reference 27 discloses an assay for simultaneous detection and differentiation of human polyomaviruses JC and BK by a rapid and sensitive PCR-ELAHA method. Detection of porcine circoviruses in human cell lines by PCR and indirect immune fluorescence assays is disclosed in reference 28. PCR methods for birnavirus detection are disclosed in references 29 & 30.

The detection method of the invention may be performed at any stage(s) during vaccine manufacture, starting from the seed virus and/or the cell substrate and/or the culture medium, through the viral infection and growth stages, through viral harvest, through any viral processing (e.g. splitting and/or surface protein extraction), through vaccine formulation and then to vaccine packaging. Thus the assay used according to the invention can be performed on the materials used to create the viral culture, on the viral culture itself, and on material extracted and derived from the viral culture. The assay need not be performed on each and every vaccine or culture, but can be used at appropriate intervals as part of normal quality control. It is particularly useful when vaccine production is changed for the new yearly strains recommended by regulatory authorities, at which stage new cultures are established and must be subjected to new quality control. Assays of the invention are advantageously performed on the seed virus used for vaccine manufacture.

In the methods of the invention, the cell lines used to grow influenza viruses may be cultured in any suitable medium e.g. in serum-free media, in protein-free media, etc. Methods for the serum-free culture of influenza virus are disclosed in reference 2, and methods for protein-free culture are disclosed in reference and/or protein-free 31. A "protein-free" medium may, however, include one or more proteases (e.g. trypsin) that may be necessary for influenza virus propagation. A serum-free medium may include serum supplements.

It is also preferred that the vaccine should have been grown in a culture without the addition of bovine-derived material, thereby ensuring that the culture is free from any possible BSE contamination and from bovine viruses. Media that do not include components associated with any transmissible spongiform encephalopathy are preferred.

The Influenza Vaccine

The invention concerns quality control of influenza vaccines. The vaccine may be in the form of a live virus or, preferably, an inactivated virus. Virus inactivation typically involves treatment with a chemical such as formalin or β-propiolactone. Where an inactivated virus is used, the vaccine may be a whole virus, a split virus, or viral subunits. Split viruses are obtained by treating virions with detergents (e.g. ethyl ether, polysorbate 80, deoxycholate, tri-N-butyl phosphate, Triton X-100, Triton N101, cetyltrimethylammonium bromide, etc.) to produce subvirion preparations. Subunit vaccines comprise the influenza surface antigens haemagglutinin and neuraminidase. Influenza antigens can also be presented in the form of virosomes [32].

Influenza vaccines of the invention can be based on any suitable strain(s). Vaccines typically include antigens from at least one strain of influenza A virus and/or at least one strain of influenza B virus. The recommended strains for vaccines change from season to season. In the current inter-pandemic period, vaccines typically include two influenza A strains (H1N1 and H3N2) and one influenza B strain, and trivalent vaccines are preferred. The invention is also suitable for preparing viruses from pandemic strains, such as H5 or H7 strains, that is strains to which the human population is immunologically naïve. Vaccines in pandemic situations may be monovalent, or they may be based on a normal trivalent vaccine supplemented by a pandemic strain.

The influenza virus(es) used in the processes of the invention may be reassortant strains, and/or may have been obtained by reverse genetics techniques. The virus(es) may be attenuated. The virus(es) may be temperature-sensitive. The virus(es) may be cold-adapted.

Where a vaccine includes more than one strain of influenza, the different strains are typically grown separately and are mixed after the viruses have been harvested and antigens have been prepared. Thus the processes of the invention may include the step of mixing antigens from more than one influenza strain. Testing for pathogens may be performed before or after such mixing.

The vaccine will typically be prepared for administration to a patient by injection (e.g. subcutaneous injection or intramuscular injection), although other routes of administration are known for influenza vaccines e.g. intranasal [33-35], oral [36], intradermal [37,38], transcutaneous, transdermal [39], etc.

Vaccines prepared according to the invention may be used to treat both children and adults. Influenza vaccines are currently recommended for use in pediatric and adult immunisation, from the age of 6 months. Safety concerns are most acute for pediatric vaccines, particularly as immunologically naive subjects typically receive two vaccine doses in a short period (e.g. at a 1 or 2 month interval).

Vaccines of the invention may include an adjuvant. Adjuvants that have been used in influenza vaccines include aluminium salts [40,41], chitosan [42], CpG oligodeoxynucleotides such as CpG 7909 [43], oil-in-water emulsions such as MF59 [44], water-in-oil-in-water emulsions [45], E. coli heat labile toxin [34,46] and its detoxified mutants [47-48], monophosphoryl lipid A [49] and its 3-o-deacylated derivative [50], pertussis toxin mutants [51], muramyl dipeptides [52], etc.

Haemagglutinin (HA) is the main immunogen in inactivated influenza vaccines, and vaccines doses are standardised by reference to HA levels, typically as measured by a single radial immunodiffution (SRID) assay. Vaccines typically contain about 15 µg of HA per strain, although lower doses are also used e.g. for children, or in pandemic situations. Fractional doses such as ½ (i.e. 7.5 µg HA per strain), ¼ and ⅛ have been used [40,53]. Thus vaccines may include between 1 and 20 µg of HA per influenza strain, preferably e.g. about 15, about 10, about 7.5, about 5, about 3.8, about 1.9, etc.

The vaccines may include preservatives such as thiomersal or 2-phenoxyethanol. It is preferred, however, that the vaccine should be substantially free from (i.e. less than 5 µg/ml) mercurial material e.g. thiomersal-free [54,55]. Vaccines containing no mercury are more preferred.

The vaccines of the invention preferably contain less than 10 ng (preferably less than 1 ng, and more preferably less than 100 pg) of residual host cell DNA per dose, although trace amounts of host cell DNA may be present. Contaminating DNA can be removed during vaccine preparation using standard purification procedures e.g. chromatography, etc. Removal of residual host cell DNA can be enhanced by nuclease treatment e.g. by using the Benzonase™ DNase [1]. Vaccines containing <10 ng (e.g. <1 ng, <100 pg) host cell DNA per 15 µg of haemagglutinin are preferred, as are vaccines containing <10 ng (e.g. <1 ng, <100 pg) host cell DNA per 0.25 ml volume. Vaccines containing <10 ng (e.g. <1 ng, <100 pg) host cell DNA per 50 µg of haemagglutinin are more preferred, as are vaccines containing <10 ng (e.g. <1 ng, <100 pg) host cell DNA per 0.5 ml volume.

These various characteristics of the vaccines may be achieved by including suitable steps in the processes of the invention. Specific steps thus include: a step of inactivation; a step of mixing three virus strains to make a trivalent vaccine; a step of formulating the vaccine for injection; a step of administering the vaccine to a patient; a step of combining the vaccine with an adjuvant; a step of measuring HA content; a step of adjusting HA content e.g. by dilution; a step of adding a preservative; a step of removing residual host cell nucleic acids; etc.

Preferred Adventitious Agents for Testing

Preferred embodiments of the invention involve adventitious agents, and particularly viruses, that are found in respiratory samples, as these are more likely to be present in initial clinical isolates of influenza virus. Respiratory pathogens include: RSV, PIV-3, SARS coronavirus, adenoviruses, rhinoviruses, reovirus ('respiratory enteritic orphan virus'), etc. Herpes simplex virus can also be found in respiratory samples.

Particularly preferred pathogens for which the invention is used are: reoviruses (particularly mammalian reoviruses); polyomaviruses; birnaviruses; circoviruses; and parvoviruses. Testing for herpes simplex viruses is also preferred.

Where a vaccine has been treated with detergent (e.g. a split or a subunit vaccine) then this treatment step offers an extra degree of safety, as it can also disrupt the contaminating viruses. If the contaminant is non-enveloped, however, then the detergent treatment will usually have no effect on the vaccine, and so it does not itself improve safety. Thus testing for the following pathogens is particularly important, as they are non-enveloped: Picornaviridae, Reoviridae, Birnaviridae, Parvoviridae, Circoviridae, Adenoviridae, Polyomaviridae.

Detergent resistance of these viruses combined with their high growth in Vero cells means that it is particularly important to test for the human enteroviruses, the mammalian Reoviridae, the Adenoviridae and the Polyomaviridae when using a Vero cell substrate. The mammalian Reoviridae also grow at high levels in MDCK cells. These viruses are also among those most resistance to inactivation.

Testing for the presence of mammalian Reoviridae is a preferred embodiment of the invention, as: (a) the viruses do not readily grow in hen eggs, and so testing for them has not been part of traditional influenza virus manufacture; (b) the viruses can show unrestricted growth in both MDCK and Vero cell lines; (c) the viruses are highly resistant to inactivation and remain stable during vaccine processing; (d) the viruses are non-enveloped and so can survive detergent treatment of influenza virus; and (e) the viruses are involved in respiratory infections and so could contaminate initial viral isolates. Testing for avian Reoviridae is also important where avian materials have been used during preparation of the virus, and criteria (b) to (e) listed above apply equally to avian reoviruses.

Other Biologicals

As well as being useful for testing influenza vaccines, the invention can also be used for other biologicals, such as recombinant proteins e.g. antibodies [56], growth factors, cytokines, lymphokines, receptors, hormones, vaccine antigens, diagnostic antigens, etc.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Further general information on influenza vaccines, including strains, cell lines for growth, doses, combinations, formulations, etc. can be found in chapters 17 & 18 of reference 57. Further details on influenza virus, including details of its life cycle during viral growth, can be found in chapter 46 of reference 14.

MODES FOR CARRYING OUT THE INVENTION

MDCK Cells

The inventor has extensive experience of growing influenza viruses on MDCK cells in serum-free culture for the preparation of vaccines. They have realised that the cells are also suitable hosts for other pathogenic agents, and so the ability of various other pathogens to grow in the same conditions was tested (specifically, culture of MDCK 33016, deposited as DSM ACC2219, in serum-free medium, as disclosed in reference 2).

When testing for active virus replication or growth in MDCK cells, tests for respiratory syncytial viruses RSV-A2 and RSV-B were negative. Parainfluenzavirus strains PI-3 and SV-5 were detected. Tests for human coronaviruses 229E and SARS were negative, as were tests for poliovirus I, echovirus 6, coxsackievirus A16 and coxsackievirus B3. Type Ib, 37 and NL.9501841 rhinoviruses tested negative. Tests for reovirus Reo3 were positive, as were tests for herpes simplex virus HSV-1. Tests for human adenoviruses 1, 5 and 6 were negative. SV-40 tests were negative, and inoculum titers were stable for 14 days. Canine parvovirus and minute virus of mice tested negative, as did Rous sarcoma virus. *Mycoplasma hyorhinis* tested negative. *Chlamydia trachomatis* tested negative, although a very low level of growth could not be excluded during days 3-5 after infection.

Further investigation revealed that MDCK cells can support growth of vesicular stomatitis (Indiana) virus, vaccinia virus, coxsackievirus B5; reovirus 2; human adenovirus types 4 and 5; vesicular exanthema of swine virus, and infectious canine hepatitis virus [58].

Of the viruses which could be grown in MDCK cells, parainfluenzaviruses, herpes simplex viruses and adenoviruses can also grow in embryonated hen eggs. In contrast, the human reoviruses (and other mammalian reoviruses) do not readily grow in eggs. If MDCK is used as a cell culture system for influenza virus production, therefore, quality control testing should check for contamination by human reoviruses. The inventor estimates that reovirus levels could increase by 5 logs or more during repeated passages in MDCK suspension cultures, whereas levels of a virus such as adenovirus would decrease by 6 to 10 logs. Herpes simplex virus levels should also be checked, as HSV growth of at least 8 logs is possible. Similarly, PIV-3 growth of 8 logs has been seen after 1 week of culture.

Vero Cells

Following the testing work on MDCK cells, replication of pathogens in Vero cells was investigated. Vero cells support the growth of pathogens such as: pneumoviruses, such as RSV-A and RSV-B; human metapneumoviruses (HMPV); morbilliviruses, such as measles virus; paramyxoviruses, such as mumps virus and parainfluenza virus; rubellavirus; human and avian coronaviruses; picornaviruses, such as entroviruses, echoviruses and coxsackie viruses, and porcine SVDV and Teschen-Talfan virus; mammalian and avian reoviruses; herpesviruses, such as HSV-1 and HSV-2; simian and human adenoviruses; varicella zoster virus (VZV); polyomaviruses, such as JC, BK and SV-40; birnaviruses, such as gumborovirus; porcine circoviruses; canine parvovirus; and *Chlamydia*.

Of these pathogens, the following do not grow in hen eggs, and are thus new risks for contamination of influenza vaccines when Vero cells are used as a substrate: RSV; HMPV; measles virus; rubellavirus; human coronaviruses; enteroviruses; reoviruses; VZV; polyomaviruses; porcine picornaviruses, parvoviruses and circoviruses. Many of these pathogens do not grow in MDCK cells, showing that MDCK is a safer substrate for influenza vaccine production. Emerging viruses such as the SARS coronavirus grow on Vero cells, but not on MDCK cells. Similarly, VZV grows on Vero cells, but not on hen eggs or on MDCK cells. Vaccination with a Vero-derived influenza vaccine that was inadvertently contaminated with this coronavirus or with VZV could lead to an iatrogenic outbreak of SARS and/or chickenpox, which would be disastrous both to the population and to the reputation of vaccines. Having identified these risks, however, appropriate quality control mechanisms can be put in place.

In addition to Vero cells, PER.C6 cells support growth of adenoviruses [59,60]. Based on known viral characteristics, PER.C6 cells can also be expected to support the growth of at least parainfluenzaviruses and reoviruses.

It will be understood that the invention is described above by way of example only and modifications may be made while remaining within the scope and spirit of the invention.

REFERENCES

The Contents of Which are Hereby Incorporated by Reference

[1] U.S. Pat. No. 5,948,410.
[2] WO97/37000.
[3] Brands et al. (1999) *Dev Biol Stand* 98:93-100.
[4] Halperin et al. (2002) *Vaccine* 20:1240-7.
[5] Tree et al. (2001) *Vaccine* 19:3444-50.
[6] Kistner et al. (1998) *Vaccine* 16:960-8.
[7] Kistner et al. (1999) *Dev Biol Stand* 98:101-110.
[8] Bruhl et al. (2000) *Vaccine* 19:1149-58.
[9] Pau et al. (2001) *Vaccine* 19:2716-21.
[10] http://www.atcc.org/
[11] http://locus.umdnj.edu/
[12] WO03/076601.
[13] WO2005/042728.
[14] Knipe & Howley *Fields Virology* (4th edition, 2001). ISBN 0-7817-1832-5.
[15] Puppe et al. (2004) *J Clin Virol* 30:165-74.
[16] Leary et al. (2002) *J Clin Microbiol* 40:1368-75.
[17] Maertzdorf et al. (2004) *J Clin Microbiol* 42:981-6.
[18] Erdman et al. (2003) *J Clin Microbiol* 41:4298-303

[19] Mosquera Mdel et al. (2002) *J Clin Microbiol* 40:111-6.
[20] Deffernez et al. (2004) *J Clin Microbiol* 42:3212-3218.
[21] Coiras et al. (2004) *J Med Virol* 72:484-95.
[22] Reid et al. (2004) *J Virol Methods* 116:169-76.
[23] Poon et al. (2004) *J Clin Virol* 30:214-7.
[24] Campsall et al. (2004) *J Clin Microbiol* 42:1409-13.
[25] Huang et al. (2004) *Vet Microbiol* 101:209-14.
[26] Mayall et al. (2003) *J Clin Pathol* 56:728-30.
[27] Whiley et al. (2004) *J Med Virol* 72:467-72.
[28] Hattermann et al. (2004) *Xenotransplantation* 11:284-94.
[29] Novoa et al. (1995) *Vet Res* 26:493-8.
[30] Blake et al. (1995) *J Clin Microbiol* 33:835-9.
[31] WO96/15231.
[32] Huckriede et al. (2003) *Methods Enzymol* 373:74-91.
[33] Greenbaum et al. (2004) *Vaccine* 22:2566-77.
[34] Zurbriggen et al. (2003) *Expert Rev Vaccines* 2:295-304.
[35] Piascik (2003) *J Am Pharm Assoc* (Wash DC). 43:728-30.
[36] Mann et al. (2004) *Vaccine* 22:2425-9.
[37] Halperin et al. (1979) *Am J Public Health* 69:1247-50.
[38] Herbert et al. (1979) *J Infect Dis* 140:234-8.
[39] Chen et al. (2003) *Vaccine* 21:2830-6.
[40] Hehme et al. (2004) *Virus Res* 103:163-71.
[41] U.S. Pat. No. 6,372,223.
[42] U.S. Pat. No. 6,534,065.
[43] Cooper et al. (2004) *Vaccine* 22:3136-43.
[44] Frey et al. (2003) *Vaccine* 21:4234-7.
[45] Bozkir & Hayta (2004) *Drug Target* 12:157-64.
[46] Guebre-Xabier et al. (2003) *J Virol* 77:5218-25.
[47] Peppoloni et al. (2003) *Expert Rev Vaccines* 2:285-93.
[48] Pine et al. (2002) *J Control Release* 85:263-70.
[49] Baldridge et al. (2000) *Vaccine* 18:2416-25.
[50] WO94/19013.
[51] EP-A-0721782.
[52] U.S. Pat. No. 5,292,506.
[53] WO01/22992.
[54] Banzhoff (2000) *Immunology Letters* 71:91-96.
[55] WO02/097072.
[56] Adamson (1998) *Dev Biol Stand* 93:89-96.
[57] *Vaccines*. (eds. Plotkin & Orenstein) 4th edition, 2004. ISBN 0-7216-9688-0.
[58] ATCC catalog information for MDCK (CCL 34).
[59] Goossens et al. (2001) *Arthritis Rheum* 44:570-7.
[60] Fallaux et al. (1998) *Hum Gene Ther* 9:1909-17.

What is claimed:

1. A process for preparing a therapeutic or vaccine comprising a biological selected from a vaccine antigen, an antibody, a growth factor, a cytokine, a lymphokine, a receptor, and a hormone, from a culture of a PER.C6 cell line, comprising (i) testing for the presence of a parainfluenzavirus or an orthoreovirus of the mammalian Reoviridae, (a) during manufacture of the therapeutic or vaccine, and/or (b) in a seed, the therapeutic or vaccine, the culture, or combinations thereof, and (ii) formulating the therapeutic or vaccine manufactured from the biologic obtained from the culture of the PER.C6 cell line, wherein the testing is performed before, during and/or after the formulating.

2. The process of claim 1, wherein testing is performed at one of the following stages of manufacture: infection, growth stages, harvest, processing, splitting, surface protein extraction, therapeutic or vaccine formulation, and therapeutic or vaccine packaging.

3. The process of claim 1, wherein the vaccine is an inactivated influenza vaccine prepared from an influenza virus propagated in the PER.C6 cell line and the testing during manufacture is performed by obtaining a sample during one or more of viral infection, growth stages, viral harvest, viral processing, splitting, surface protein extraction, vaccine formulation, and vaccine packaging.

4. The process of claim 1, wherein testing is performed on the seed, the therapeutic or vaccine, the culture, or combinations thereof.

5. The process of claim 1, wherein the testing of step (i) is for an adventitious agent.

6. A process for preparing a therapeutic or vaccine comprising a biological selected from a vaccine antigen, an antibody, a growth factor, a cytokine, a lymphokine, a receptor, and a hormone, from a culture of a PER.C6 cell line, comprising (i) culturing the culture of the PER.C6 cell line, and (ii) formulating the therapeutic or vaccine manufactured from the biological obtained from the culture of the PER.C6 cell line, wherein testing for the presence of a parainfluenzavirus or an orthoreovirus of the mammalian Reoviridae was performed (a) during manufacture of the therapeutic or vaccine, and/or (b) on a seed, the cell substrate, the culture, or combinations thereof, and the testing was performed before or during the formulating.

7. The process of claim 6, wherein testing was performed at one of the following stages of manufacture: infection, growth stages, harvest, processing, splitting, surface protein extraction, and therapeutic or vaccine formulation.

8. The process of claim 6, wherein the vaccine is an inactivated influenza vaccine prepared from an influenza virus propagated in the PER.C6 cell line and the testing during manufacture was performed by obtaining a sample during one or more of viral infection, growth stages, viral harvest, viral processing, splitting, surface protein extraction, and vaccine formulation.

9. The process of claim 6, wherein testing was performed on the seed, the culture, or combinations thereof.

10. The process of claim 6, wherein testing was performed by immunochemical detection and/or nucleic acid detection.

11. The process of claim 10, wherein the immunochemical detection, if used, was by ELISA and the nucleic acid detection, if used, was performed by PCR (including RT-PCR).

12. The process of claim 8, further comprising one of more of the following steps: a step of administering the vaccine to a patient; a step of combining the vaccine with an adjuvant; and a step of measuring HA content.

13. The process of claim 8, wherein the vaccine is a trivalent influenza vaccine.

14. The process of claim 8, wherein the vaccine includes a pandemic influenza vaccine.

15. The process of claim 14, wherein the vaccine includes a H5 or H7 influenza virus strain.

16. The process of claim 8, wherein the vaccine is a whole virus vaccine, a split virus vaccine, or a viral subunit vaccine.

17. The process of claim 9, wherein the culture tested was (i) the culture itself, (ii) material extracted from the culture, or (iii) the biological harvest.

18. The process of claim 6, wherein the biological is a recombinant protein produced by the PER.C6 cell line.

19. The process of claim 18, further comprising one of more of the following steps: a step of formulating the therapeutic for injection; a step of administering the therapeutic to a patient; a step of adding a preservative; and a step of removing residual host cell nucleic acids.

20. The process of claim 6, wherein the testing was for the presence of an adventitious agent.

\* \* \* \* \*